United States Patent [19]
Brown

[11] Patent Number: 5,959,455
[45] Date of Patent: Sep. 28, 1999

[54] FLUID CONDUCTIVELY SENSOR

[75] Inventor: Neil L. Brown, Falmouth, Mass.

[73] Assignee: Falmouth Scientific, Inc., Cataumet, Mass.

[21] Appl. No.: 08/944,263

[22] Filed: Oct. 6, 1997

[51] Int. Cl.[6] .................................................. G01R 27/22
[52] U.S. Cl. ........................... 324/445; 324/715; 324/695
[58] Field of Search .................................... 324/445, 695, 324/696, 715

[56] References Cited

U.S. PATENT DOCUMENTS

| | | |
|---|---|---|
| 3,603,873 | 9/1971 | Cirulis . |
| 3,980,946 | 9/1976 | Fleury . |
| 4,740,755 | 4/1988 | Ogawa . |
| 5,252,925 | 10/1993 | Matsumoto et al. . |
| 5,341,102 | 8/1994 | Akiyama et al. . |

FOREIGN PATENT DOCUMENTS

| | | | |
|---|---|---|---|
| 1129232 | 2/1960 | Germany .............................. | 324/445 |
| 644629 | 9/1962 | Italy ....................................... | 324/445 |
| 2093192 | 8/1982 | United Kingdom ................... | 324/445 |

*Primary Examiner*—Josie Ballato
*Assistant Examiner*—Jose Solis
*Attorney, Agent, or Firm*—Henry D. Pahl, Jr.; Peter J. Manus

[57] ABSTRACT

The fluid conductivity sensor disclosed herein is adapted for the non-contacting measurement of fluid conductivity and utilizes first and second insulating tubes, each of which is provided with both the driving transformer and the sensing transformer. The sensor is immersed in the fluid to be tested so that the tubes fill with the fluid. The driving transformer's are oppositely poled so that the current induced in one tube tends to return through the other tube. Shrouds are provided which link the corresponding ends of the tubes and operate to obstruct in-fluid current flow not linking both of the tubes. Accordingly the influence of objects nearby in the fluid is substantially eliminated.

6 Claims, 3 Drawing Sheets

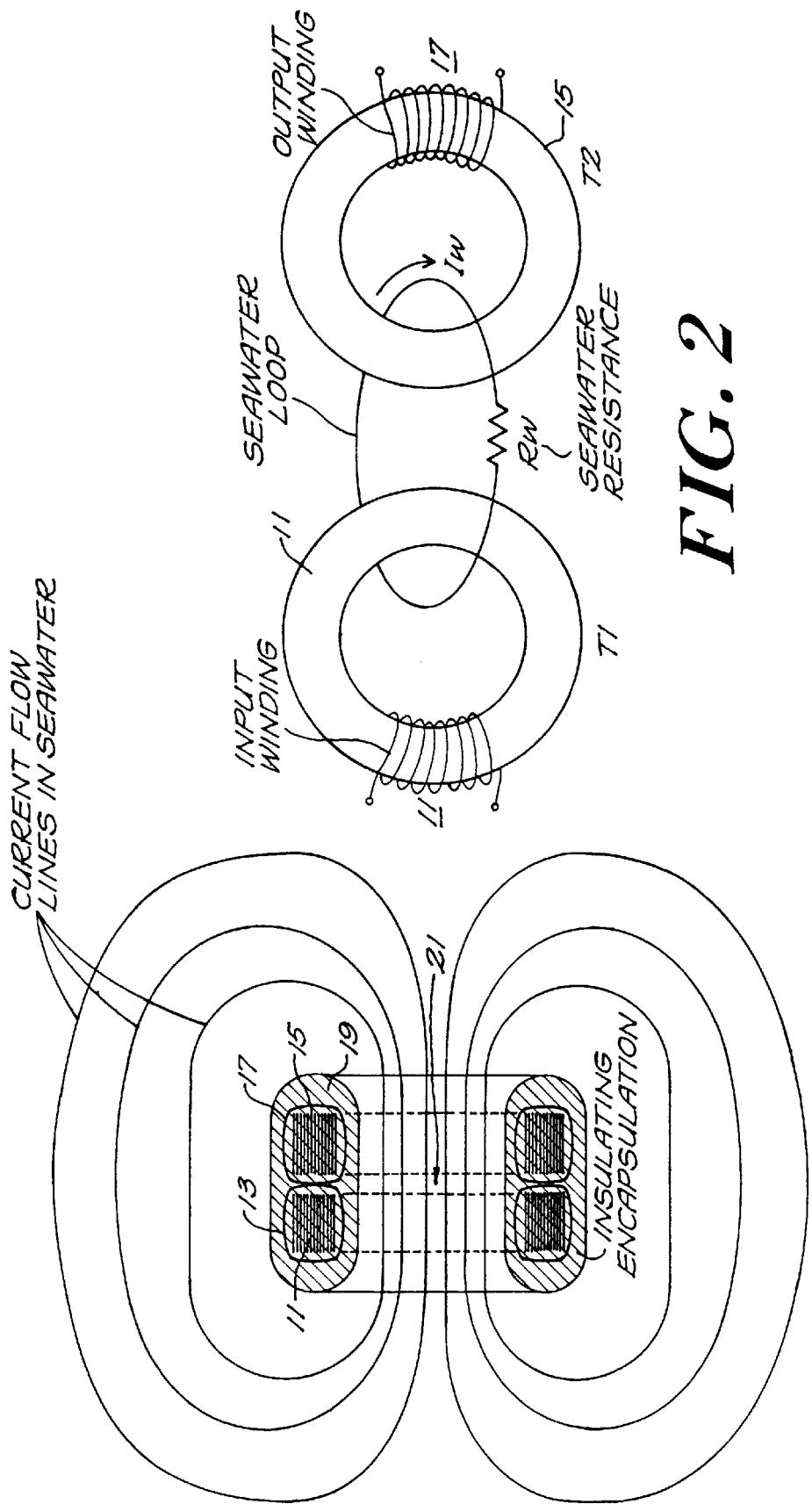

FLUID CONDUCTIVELY SENSOR

BACKGROUND OF THE INVENTION

The present invention relates to fluid conductivity sensors, and more particularly to a non-contacting fluid conductivity sensor which generates essentially no external current field and thus is not influenced by nearby objects in the fluid in which the sensor is immersed.

Industrial process control systems often require the measurement of the electrical conductivity of a fluid e.g. seawater, used in the system. Sensors for fluid conductivity measurement usually fall into one of two categories, i.e, contacting sensors and non-contacting sensors. Contacting sensors rely on a direct electrical contact between the measurement electronics and the material to the fluid, while non-contacting sensors typically employ driving and sensing transformers which, respectively, induce and measure a flow of current in the conductive fluid, the measurement of the induced current being a function of the conductivity of fluid. One problem which has existed with existing non-contacting conductivity sensors is that they may be influenced by objects a considerable distance from the sensor in the body of fluid into which the sensor is immersed. This influence is caused by the fact that conventional, immersible sensors typically have an external current field which extends a substantial distance from the sensor in the fluid in which the sensor is immersed. This is a significant problem in that calibration performed initially in the calibration laboratory will not be the same as calibration in the field.

SUMMARY OF THE PRESENT INVENTION

The fluid conductivity sensor of the present invention employs first and second tubes constructing of an insulating material. Around each of the tubes is provided a respective magnetic core and driving winding for inducing a current in a conductive fluid linking that tube. The driving windings on the two tubes are oppositely poled. Each of the tubes is also provided with a second magnetic core having an output winding. Shrouds are provided linking adjacent ends of the tubes, the shrouds being operative to obstruct in-fluid current flow which does not link both of the tubes.

BRIEF DESCRIPTION OF THE DRAWINGS

FIG. 1 is a view, partially in section, of a prior art fluid conductivity sensor;

FIG. 2 is a diagram illustrating the basic mode of operation of the sensor of FIG. 1;

Corresponding reference characters indicate corresponding parts throughout the several views of the drawings.

DESCRIPTION OF THE PREFERRED EMBODIMENT

Figure 3:
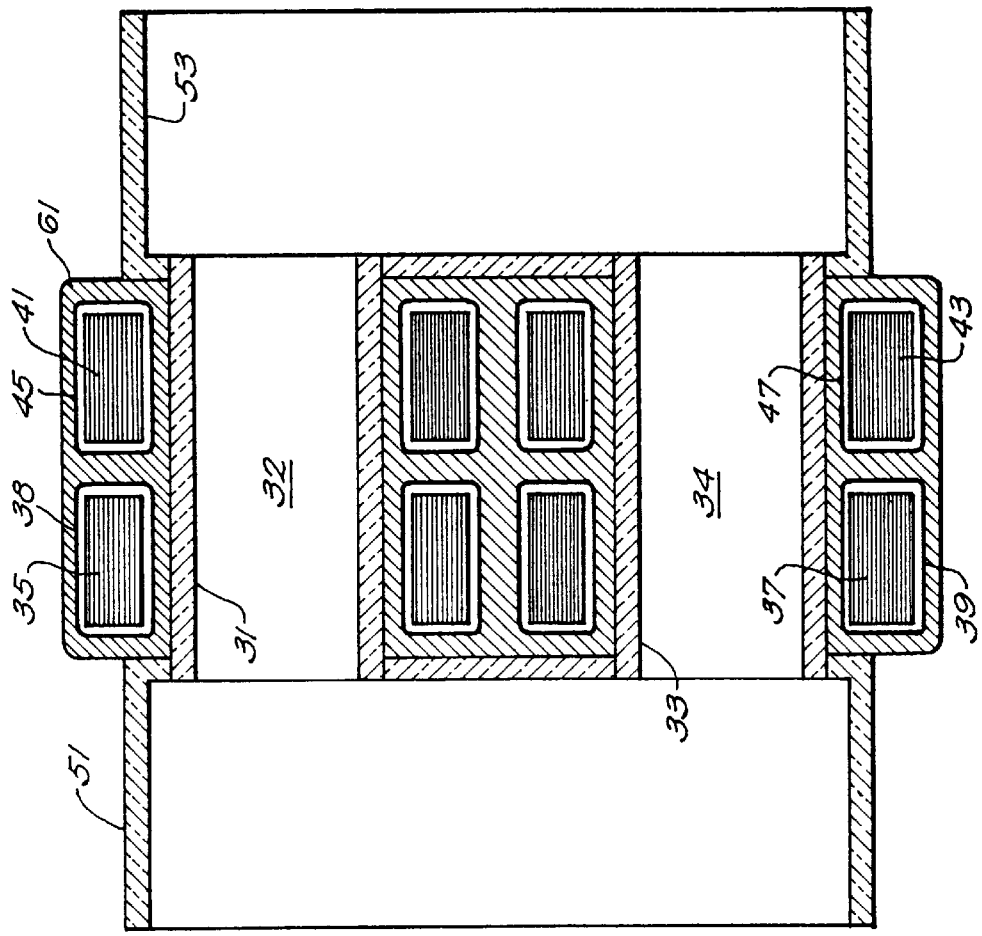
FIG. 3 is a side view in section of a fluid conductivity sensor in accordance with the present invention.

Referring now to FIG. 1 which illustrates a prior art type of non-contacting conductivity sensor, it may be seen that the sensor employs a first magnetic core 11 provided with a toroidal driving or input winding 13. The sensor also employs a second core 15 with an output or sensing winding 15. The two cores are aligned and coaxial and potted in an incapsulating material 19 with an open central area 21 so that, when the sensor is immersed in a conductive liquid, e.g. sea water, a current path through liquid is established which links the two magnetic cores 11 and 15. Accordingly, when an AC voltage is applied to the winding 13, a current will be induced in the conductive liquid, which current also links the core 15 so that a corresponding current is induced in the output winding 17.

The equivalent circuit is illustrated in FIG. 2, where the current path linking the two cores 11 and 15 is shown as including a resistance $R_w$ which represents the sea water resistance, which is in turn a function of the conductivity of the sea water. Accordingly, the current induced in the output or sensing winding 17 is variable as the function of the conductivity of the liquid. However, as is illustrated in FIG. 1, the current flow in the sea water extends, though at diminished intensity, for a considerable distance from the sensor itself. Accordingly, objects in liquid can influence the actual value of $R_W$, either by displacing conductive liquid or by being more conductive than the liquid itself.

Figure 4:
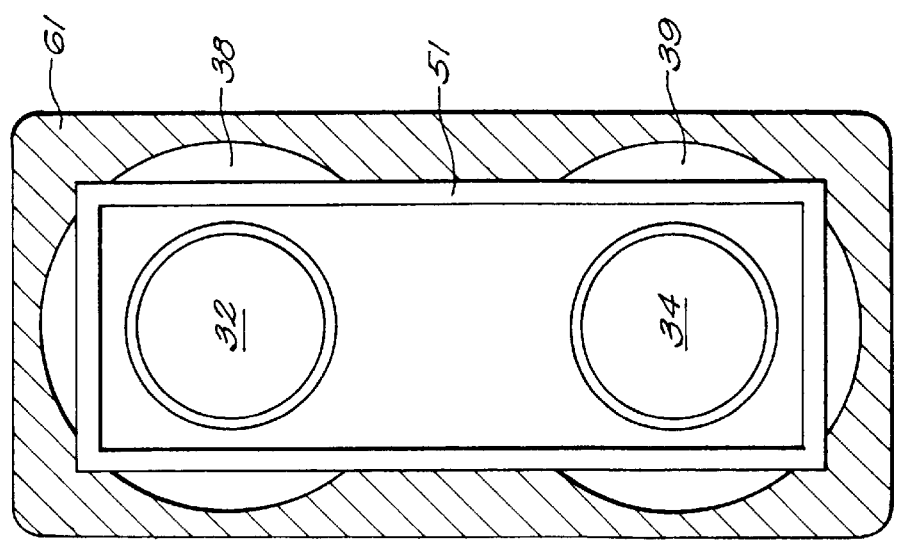
FIG. 4 is an end view of the sensor of FIG. 3.

In the sensor of the present invention illustrated in FIGS. 3 and 4, there are two tubes 31 and 33 constructed of a suitable insulating material, e.g. a non-conductive ceramic. The tubes provide open central spaces, 32 and 34 respectively, of circular cross-section. As is explained in greater detail hereinafter, the tubes are intended to be open to or immersed in the fluid whose conductivity is to be measured. The two tubes are similar and preferably essentially identical so that the fluid paths in the two tubes are essentially parallel and will exhibit the same resistance end to end.

Each of the tubes 31 and 33 is provided with a first surrounding magnetic core, 35 and 37 respectively, and each of these cores is provided with a respective input or driving winding, 38 and 39 respectively. Each of the tubes 31 and 33 is also provided with a second core, 41 and 43 respectively, having an output or sensing winding, 45 and 47 respectively. The windings are preferably toroidally wound on high permeability tape wound cores. An encapsulating material is provided as indicated at 61.

In operation the driving windings 38 and 39 on the two tubes are oppositely poled so that the current induced by one of the windings in the conductive fluid in the respective tube will tend to return through the other tube. In other words, when both the driving windings are energized, they will tend to aid each other in inducing a current which links both of the tubes. While the present invention is concerned principally with the design of the sensor itself, which can be used with a variety of prior art driving and sensing circuits, it is preferred that it the driving and sensing circuitry be of the compensated feedback type described in coassigned U.S. Pat. No. 5,455,513 issued Oct. 3, 1995 to Neil L. Brown and Alan J. Fougere. While the outputs of the two sensing windings may be separately measured and the results summed, it will typically be sufficient to connect the two windings in series so their outputs add.

The adjacent left hand ends of the tubes 31 and 33 are linked or coupled by a box-like shroud 51, which is also constructed of an insulating material such as a non-conductive ceramic. The right hand ends of the tubes 31 and 33 are coupled by a similar shroud 55. The shrouds 51 and 55 operate to obstruct any stray current which might tend to flow out into the surrounding body of fluid into which the sensor is immersed, such as might be caused by second order effects, e.g. the slight drop in potential between the adjacent ends of the two tubes.

Figure 5:
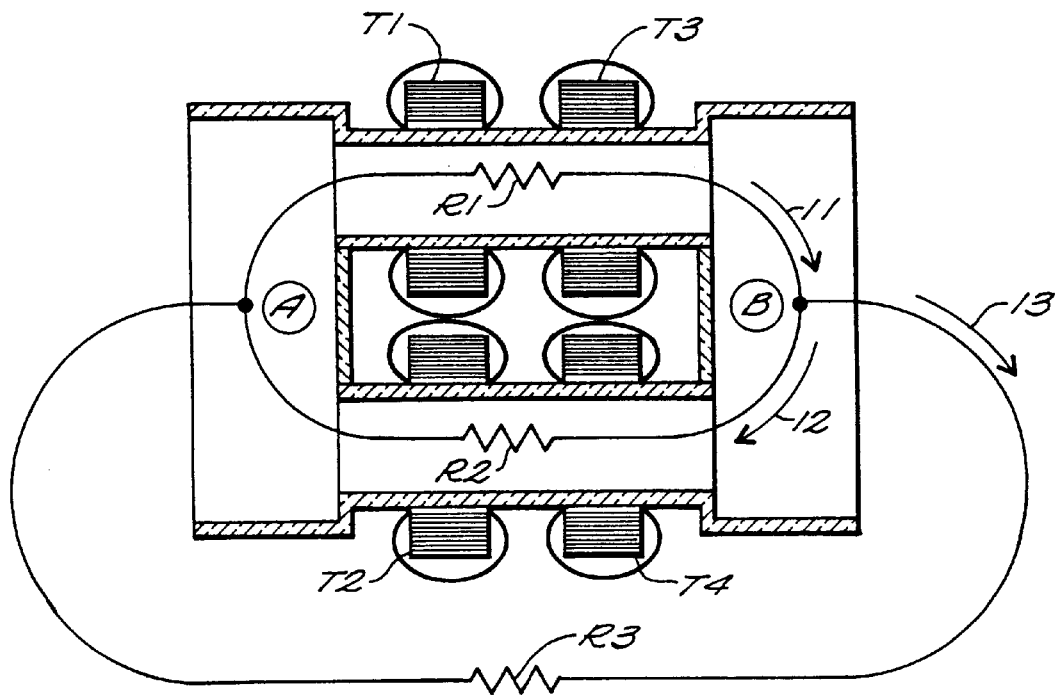
FIG. 5 is a diagram illustrating the equivalent resistances and current's operative in the sensor of FIGS. 3 & 4.
Figure 6:
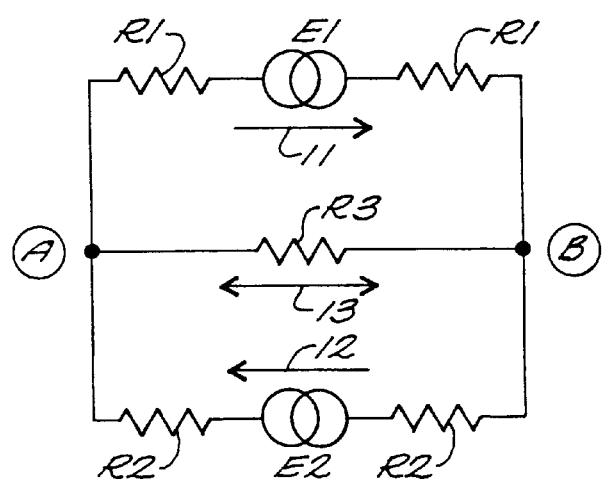
FIG. 6 is a circuit diagram reflecting similar resistances and currents.

FIG. 5 illustrates the possible current paths through the conductive liquid and the resistances associated with each. FIG. 6 is a circuit diagram of the equivalent circuit showing the voltages induced in the conductive liquid by the driving windings 38 and 39. Points A and B designate the potential at the middle point in the body of liquid occupying each of the shrouds 51 and 55 respectively. In FIG. 6, resistors are R1 and R2 represent the resistances from A to B via the upper tube and lower tube respectively. Resistor R3 represents the resistance from A to B via the liquid fluid path external to the sensor structure. The voltages E1 and E2 represent the voltages induced by the windings 38 and 39. $I_1$ and $I_2$ are the resulting currents flowing in the upper and lower tubes.

It can be shown that if the ratio R1/E1 is equal to the ratio R2/E2 then I1 will be equal to I2. If the directions of I1 and I2 are opposite, then the difference which flows externally will be zero. This means that the external effects will be zero. Since the seawater in the two tubes has the same conductivity and the dimensions are the same then the two resistances R1 and R2 are the same. Transformers T1 and T2 have identical windings and are connected the same voltage, hence E1 and E2 are assured of being equal. The proof is as follows. If we assume that the potential at A is zero then the following equations apply.

$$Eb = E1 * \frac{\frac{R2*R3}{R2+R3}}{R1 + \frac{R2*R3}{R2+R3}} + E2 * \frac{\frac{R1*R3}{R1+R3}}{R2 + \frac{R1*R3}{R1+R3}}$$

$$= E1 * \frac{R2*R3}{R1*R2 + R1*R3 + R2*R3} + E2 * \frac{R1*R3}{R1*R2 + R1*R3 + R2*R3}$$

$$= \frac{E1}{R1} * K + \frac{E2}{R2} * K$$

$$\text{Where } K = \frac{R1*R2*R3}{R1*R2 + R1*R3 + R2*R3}$$

If E1=−E2 and R1=R2 then it is obvious that the above equations equate to zero and that the voltage across R3 (i.e. the external path) is zero.

In practice it may not be possible to insure that the two tubes are identical. In this case the ratio of E1 to E2 can be adjusted to compensate for the inequality of R1 and R2 to maintain zero external field, e.g. by providing slightly different levels of excitation to the two driving windings.

In view of the foregoing it may be seen that several objects of the present invention are achieved and other advantages results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. A fluid conductivity sensor comprising:

first and second tubes constructed of an insulating material, said tubes providing generally similar and electrically parallel internal paths;

around each of said tubes a respective first magnetic core provided with a driving winding for inducing a current in a conductive fluid linking that tube, said driving windings being oppositely poled;

around each of said tubes a respective second magnetic core provided with an output winding for sensing current in a conductive fluid linking that tube;

at least one shroud linking adjacent ends of said tubes, said shroud being operative to obstruct in-fluid current flow not linking both of said tubes thereby to reduce the influence of objects in a fluid in which said sensor is immersed on induced currents sensed by said output windings.

2. A sensor as set forth in claim 1 wherein said tubes are parallel and essentially identical.

3. A sensor as set forth in claim 2 wherein said tubes are constructed of a non-conducting ceramic.

4. A fluid conductivity sensor comprising:

first and second similar tubes constructed of an insulating material and adapted to be immersed in a conductive fluid so as to provide a conductive path linking both tubes;

around each of said tubes a respective first magnetic core provided with a driving winding for inducing a current in a conductive fluid linking that tube, said driving windings being oppositely poled;

around each of said tubes a respective second magnetic core provided with an output winding for sensing current in a conductive fluid linking that tube;

a first shroud linking one end of each of said tubes; and a second shroud linking the other ends of said tubes, said shrouds being operative to obstruct in-fluid current flow not linking both of said tubes thereby to reduce the influence of objects in a fluid in which said sensor is immersed on induced currents sensed by said output windings.

5. A sensor as set forth in claim 4 wherein said tubes are parallel, essentially identical and provide a central opening of circular cross-section.

6. A sensor as set forth in claim 5 wherein said windings are wound toroidally on said cores and said cores are tape wound of a high permeability magnetic material.

\* \* \* \* \*